(12) United States Patent
Nawroth et al.

(10) Patent No.: US 6,930,094 B1
(45) Date of Patent: Aug. 16, 2005

(54) TISSUE FACTOR FOR INFLUENCING BLOOD VESSEL FORMATION

(75) Inventors: Peter Nawroth, Tübingen (DE); Katsumi Nakagawa, Kyoto (JP); Youming Zhang, Dresden (DE)

(73) Assignee: Merckle GmbH, Ulm (DE)

( * ) Notice: Subject to any disclaimer, the term of this patent is extended or adjusted under 35 U.S.C. 154(b) by 0 days.

(21) Appl. No.: 09/423,712

(22) PCT Filed: May 8, 1998

(86) PCT No.: PCT/DE98/01306

§ 371 (c)(1),
(2), (4) Date: Aug. 25, 2000

(87) PCT Pub. No.: WO98/51321

PCT Pub. Date: Nov. 19, 1998

Related U.S. Application Data

(63) Continuation of application No. PCT/DE98/01278, filed on May 7, 1998.

(30) Foreign Application Priority Data

May 9, 1997 (DE) .......................................... 197 19 652

(51) Int. Cl.$^7$ ........................ A61K 48/00; C12N 15/74; C12N 5/02; C12N 15/09
(52) U.S. Cl. ................... 514/44; 424/93.21; 435/320.1; 435/325; 435/455
(58) Field of Search ..................... 514/44; 424/93.21; 435/320.1, 325, 455

(56) References Cited

U.S. PATENT DOCUMENTS 5,100,792 A * 3/1992 Sanford et al. .......... 435/172.1
6,093,399 A * 7/2000 Thorpe et al. .............. 424/182
6,120,799 A * 9/2000 McDonald et al. ......... 424/450

FOREIGN PATENT DOCUMENTS

WO  WO 94/05328 A  3/1997
WO  WO 98/34634 A  8/1998

OTHER PUBLICATIONS

Robbins et al, Pharmcol Ther 1998;80:35–47.*
Miller et al, Hum Gene Ther May 1997;8:803–15.*
TW Dubensky, Jr. et al., Journal of Virology,"Sindbis Virus DNA–Based Expression Vectors:Utility for In Vitro and In Vivo Gene Transfer," Jan. 1996, vol. 70, No. 1, pp. 508–519.*
IM Verma et al., Nature, "Gene therapy–promises, problems and prospects,"Sep. 1997, vol. 389, pp. 239–242.*
F Levine et al., Molecular Medicine Today,"Towards gene therapy of diabetes mellitus," Apr. 1999, vol. 5, pp. 165–171.*
Judah Folkman, "Tumor Angiogenesis and Tissue Factor", Nature Medicine, vol. 2, No. 2, Feb. 1996, pp. 167–168, Nature Publishing Group, New York, New York, USA.
Vickie Brower, "Genentech Enlightens other Angiogenesis Programs", Nature Biotechnology, vol. 17, Apr. 1988, pp. 326–327, Nature Publishing Group, New York, New York, USA.

(Continued)

*Primary Examiner*—Q. Janice Li
(74) *Attorney, Agent, or Firm*—Burns, Doane, Swecker & Mathis, L.L.P.

(57) ABSTRACT

The present invention relates to the use of tissue factor for influencing blood vessel formation, particularly for activating blood vessel formation, above all for wound healing.

15 Claims, 5 Drawing Sheets

OTHER PUBLICATIONS

Nicola Semeraro et al., "Tissue Factor in Health and Disease", Thrombosis and Haemostasis, vol. 78, No. 1, 1997, pp. 759–764, F.K. Schattauer Verlagsgesellschaft mbH, Stuttgart, Germany.

Banner, D.W. et al., "The crystal structure of the complex of blood coagulation factor VIIa with soluble tissue factor", Nature, 1996, pp. 21–23, vol. 380, No. 6569, Nature Publishing Group, Hampshire, United Kingdom.

Bazan, J.F., "Structural design and molecular evolution of a cytokine receptor superfamily", Proc. Natl. Acad. Sci. USA, 1990, pp. 6934–6938, vol. 87, National Academy of Sciences, Washington, D.C., USA.

Camerer, E. et al., "Cell Biology of tissue factor, the principal initiator of blood coagulation", Thromb Res, 1996, p. 1–41, vol. 81, No. 1, Elsevier Science, London, United Kingdom.

Edgington, T.S. et al., "The structural biology of expression and function of tissue factor" Thromb Res, 1991, pp. 67–69, vol. 66, No. 1, Elsevier Science, London, United Kingdom.

Gibbs, C.S. et al., "Identification of the Factor VIIa binding site on Tissue Factor by homologous loop swap and alanine scanning mutagenesis", Biochemistry, 1994, pp. 14003–14010, vol. 33, American Chemical Society, Washington, D.C., USA.

Harlos, K. et al., "Crystal structure of the extracellular region of human tissue factor" Nature, 1994, pp. 662–666, vol. 370, No. 6491, Nature Publishing Group, Hampshire, United Kingdom.

Hasselbacher, C.A. et al., "Environments of the four tryptophans in the extracellular domain of human tissue factor: comparison of results from absorption and fluorescence difference spectra of tryptophan replacement mutants with crystal structure of the wild–type protein", Biophys J, 1995, pp. 20–29, vol. 69, No. 1, Stanford University Libraries'HighWire Press, Stanford, CA, USA.

Huang, X. et al., "Tumor infarction in mice by antibody–directed targeting of tissue factor to tumor vasculature", Science, 1997, pp. 547–550, vol. 275, No. 5299, Association for the Advancement of Science with the assistance of Stanford University Libraries'HighWire Press, Stanford CA, USA.

Mackman, N, "Regulation of the Tissue Factor gene" FASEB J, 1995, pp. 883–639, vol. 9, The Federation of American Societies for Experimental Biology, Bethesda, MD, USA.

Mackman, N. et al., "Complete sequence of the human Tissue Factor gene, a highly regulated cellular receptor that initiates the coagulation protease cascade", Biochemistry, 1989, pp. 1755–1762, vol. 28, American Chemical Society, Washington, D.C., USA.

Muller, Y.A. et al., "The crystal structure of the extracellular domain of human tissue factor refined to 1.7 A resolution", J Mol Biol, 1996, pp. 144–159, vol. 256, No. 1, Academic Press, San Diego, CA, USA.

O'Brien, D.P. et al., "Structural requirements for the interaction between tissue factor and factor VII: characterisation of chymotrypsin–derived tissue factor polypeptides" Biochem J, 1993, pp. 7–12, vol. 292, Portland Press, Portland, OR, USA.

Paborsky, L.R. et al., "Lipid association, but not the trans-membrane domain, is required for Tissue Factor activity", The Journal of Biological Chemistry, 1991, pp. 21911–21916, vol. 266, No. 32, American Society for Biochemistry and Molecular Biology, Bethesda, MD, USA.

Ruf, W. et al., "Two sites in the tissue factor extracellular domain mediate the recognition of the ligand factor VIIa", Proc Natl Acad Sci USA, 1991, pp. 8430–8434, vol. 88, No. 19, National Academy of Sciences, Washington, D.C., USA.

Ruf, W. et al., "Antibody mapping of tissue factor implicates two different exon–encoded regions in function", Biochem J, 1991, pp. 729–733, vol. 278, Portland Press, Portland, OR, USA.

Ruf, W. et al., "Phospholipid–independent and dependent interactions required for Tissue Factor Receptor and cofactor function", Journal of Biol Chem, 1991, pp. 2158–2166, vol. 266, No. 4, American Society for Biochemistry and Molecular Biology, Bethesda, MD, USA.

Ruf, W. et al., "Mutational mapping of functional residues in tissue factor identification of factor VII recognition determinants in both structural modules of the predicted cytokine receptor homology domain", Biochemistry, 1994, pp. 1565–1572, vol. 33, No. 6, American Chemical Society, Washington, D.C., USA.

Schullek, J.R. et al., "Key ligand interface residues in tissue factor contribute independently to factor VIIa binding", J Biol Chem, 1994, pp. 19399–19403, vol. 269, No. 30, American Society for Biochemistry and Molecular Biology, Bethesda, MD, USA.

Spicer, EK. et al., "Isolation of cDNA clones coding for human tissue factor primary structure of the protein and cDNA", Proc Natl Acad Sci USA, 1987, pp. 5148–5152, vol. 84, No. 15, National Academy of Sciences, Washington, D.C., USA.

Carmeliet et al., 1996, "Role of tissue factor in embryonic blood vessel development," *Nature* 383(6595):73–75.

Contrino et al., 1996, "In situ detection of tissue factor in vascular endothelial cells: correlation with the malignant phenotype of human breast disease," *Nat. Med.* 2(2):209–215.

Nakagawa et al., 1998, "The angiogenic effect of tissue factor on tumors and wounds," *Semin. Thromb. Hemost.* 24(3):207–210.

Scarpati et al., 1987, "Human tissue factor: cDNA sequence and chromosome localization of the gene," *Biochemistry* 26(17):5234–5238.

Shoji et al., 1996, "Tissue factor regulates the expression of vascular endothelial growth factor (VEGF) in vitro and angiogenesis in vivo," *Blood* 88(10 Suppl 1):514a.

Shoji et al., 1997, "Molecular mechanisms linking thrombosis and angiogenesis in cancer," *Trends in Cardiovascular Medicine* 7(2):52–59.

Toomey, et al., 1996, "Targeted disruption of the murine tissue factor gene results in embryonic lethality," *Blood* 88 (5):1583–1587.

Wilcox et al., 1989, "Localization of tissue factor in the normal vessel wall and in the atherosclerotic plaque," *Proc. Natl. Acad. Sci. U.S.A.* 86(8):2839–2843.

Zhang et al., 1994, "Tissue factor controls the balance of angiogenic and antiangiogenic properties of tumor cells in mice," *J. Clin. Invest* 94(3):1320–1327.

Bellon et al., "Aerosol administration of a recombinant adenovirus expressing CFTR to cystic fibrosis patients: a phase I clinical trial.", Hum Gene Ther., 1997, 8(1):15–25; Mary Ann Liebert, Inc., Larchmont, New York (Abstract only).

Crombleholme, "Adenoviral–mediated gene transfer in wound healing.", Wound Repair Regen., Nov.–Dec., 2000; 8(6):460–72; Blackwell Publishing, Oxford, England (Abstract only).

Kay et al., "Evidence for gene transfer and expression of factor IX in haemophilia B patients treated with an AAV vector.", Nat. Genet. 2000, 24(3):201–2, 2000, Nature Publishing Group, London, England (Abstract only).

Magovern et al., "Primary inflammatory fibrosarcoma of the esophagus", Ann Thorac Surg., 1996, 62(6):1848–50, Elsevier Science, Inc., New York (Abstract only).

Merrouche et al., "Clinical application of retroviral gene transfer in oncology: results of a French study with tumor–infiltrating lymphocytes transduced with the gene of resistance to neomycin.", J Clin Oncol, 1995; 13(2):410–8; American Society of Clinical Oncology, Alexandria, Virginia (Abstract only).

Miles et al., "Prostate–specific antigen response and systemic T cell activation after in situ gene therapy in prostate cancer patients failing radiotherapy.", Hum Gene Ther., Nov., 2001, 12(16):1955–67, Mary Ann Liebert, Inc., Larchmont, New York(Abstract only).

Morrissey et al., "Molecular cloning of the cDNA for tissue factor, the cellular receptor for the initiation of the coagulation protease cascade", Cell, Jul. 3, 1987, 50(1):129–35, Cell Press, Cambridge, England, (Abstract only).

Mühlhauser et al., "VEGF$_{165}$ Expressed by a Replication–Deficient Recombinant Adenovirus Vector Induces Angiogenesis In Vivo", Circulation Research, 1995, 77:1077–1086; Lippincott, Williams and Wilkins, Baltimore, Maryland.

Redfield et al., "A phase I evaluation of the safety and immunogenicity of vaccination with recombinant gp160 in patients with early human immunodeficiency virus infection.", N Engl J Med., 1991: 324(24):1677–84; Mass Medical Society, Boston, Massachusetts (Abstract only).

Sylvester et al., "Adenoviral–mediated gene transfer in wound healing: acute inflammatory response in human skin inthe SCID mouse model", Wound Repair Regen, Jan.–Feb., 2000, vol. 8, Issue 1, p. 36; Blackwell Publishing, Oxford, England (Abstract only).

Tan et al., "IL–2 gene therapy of advanced lung cancer patients.", Anticancer Res., Jul.–Aug., 1996; 16(4A):1993–8; International Conference of Anticancer Research, Attiki, Greece (Abstract only).

Verma et al., "Gene therapy—promises, problems and prospects", Nature (1997), 89, 239–242, Nature Publishing Group, London, England.

Vogt et al., "Genetically modified keratinocytes transplanted to wounds reconstitute the epidermis", Proc. Natl. Acad. Sci. USA, Sep., 1994; pp. 9307–9311, vol. 91, National Academy of Sciences, Washington, DC.

Zabner et al., "Adenovirus–mediated gene transfer transiently corrects the chloride transport defect in nasal epithelia of patients with cystic fibrosis,". Cell. 1993, 75(2):207–16, Cell Press, Cambridge, England (Abstract only).

* cited by examiner

TISSUE FACTOR FOR INFLUENCING BLOOD VESSEL FORMATION

This is a national phase filing of the Application No. PCT/DE98/01306, which was filed with the Patent Corporation Treaty on May 8, 1998, and is entitled to priority of the and is a continuation of PCT/DE98/01278 filed May 7, 1998.

FIELD OF THE INVENTION

The present invention relates to the use of issue factor for influencing blood vessel formation, particularly for activating blood vessel formation, above all for wound healing.

BACKGROUND OF THE INVENTION

The body is provided with blood by means of blood vessels. Blood vessels comprise endothelial and smooth muscle cells. In many diseases, blood vessels and the formation thereof, respectively, are impaired. This is found, e.g., in impaired wound healing as in the case of diabetes mellitus, vasculitis, arterial occlusive disease, chronic venous and infected ulcer. There are also major problems in connection with wound healing in the case of innervation impairment such as paraplegia, leprosy, neuropathy, etc., and decubital gangrene of persons in need of care. Also known are weak sutures and wound healing impairment in the case of operations, particularly of the intestines and transplantations of skin or other organs, respectively. Up to the present, there are no satisfactory products or means by which it is possible to take steps in the case of blood vessel diseases, in particular impaired wound healing.

Therefore, it is the object of the present invention to provide a product by means of which the above objective can be achieved.

SUMMARY OF THE INVENTION

The present invention relates to the use of tissue factor for influencing blood vessel formation, particularly for activating blood vessel formation, above all for wound healing.

BRIEF DESCRIPTION OF THE DRAWINGS

FIG. 2A-1 shows the formation of vessels in wounds transfected with a tissue factor-expressing vector (a). FIG. 2A-2 shows the formation of blood vessels in wounds transfected with a vector which codes for an antisense tissue factor (b). FIG. 2A-3 shows the control.

FIG. 3 shows the presence of smooth muscle cells in newly formed vessels using α-actin staining to make the vessels visible. FIG. 3A-1 shows the formation of vessels in wounds transfected with a tissue factor-expressing vector (a). FIG. 3A-2 shows the formation of blood vessels in wounds transfected with a vector which codes for an antisense tissue factor (b) FIG. 3A-3 shows the control.

DETAILED DESCRIPTION OF THE INVENTION

Figures 1A, 1B, 1C:
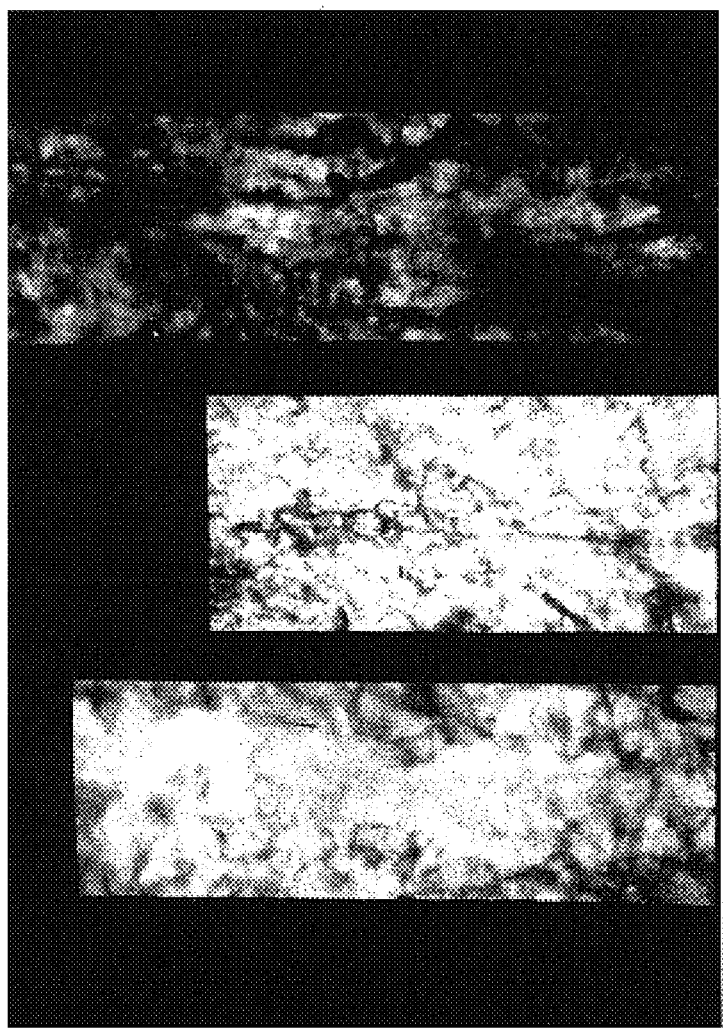
FIG. 1A shows the formation of blood vessels in wounds tranfected with a tissue factor-expressing vector (a).
FIG. 1B shows the formation of blood vessels in wounds transfected with a vector which codes for an antisense tissue factor (b).
FIG. 1C shows the control.
Figures 1, 2A:
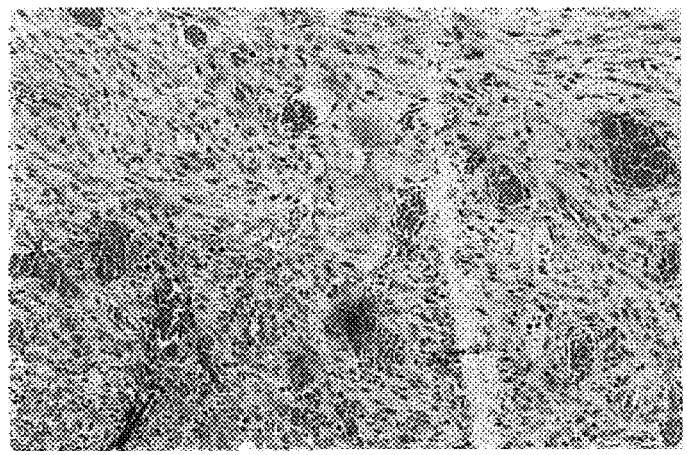
FIG. 1 shows the formation of blood-vessels in wounds transfected with a tissue factor-expressing vector.
FIG. 2A shows stains using hemtoxylin/eosin staining to make the blood vessels visible.
Figures 2, 2A:
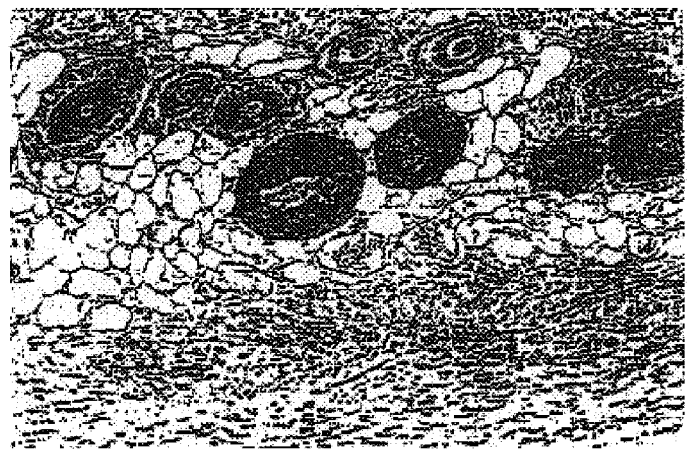
Figures 2, 2A, 3:
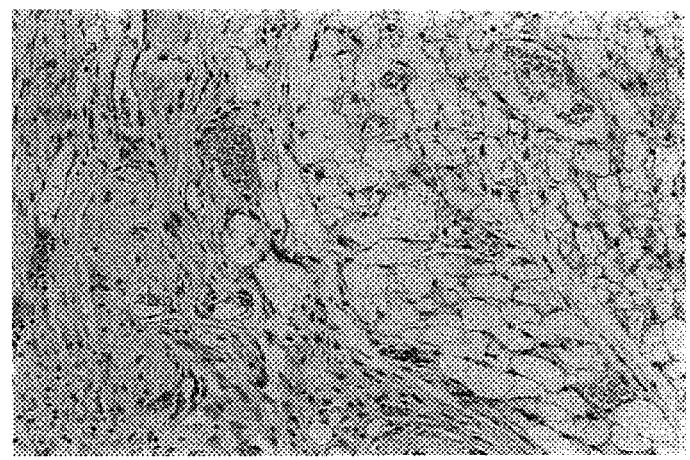
Figure 2B:
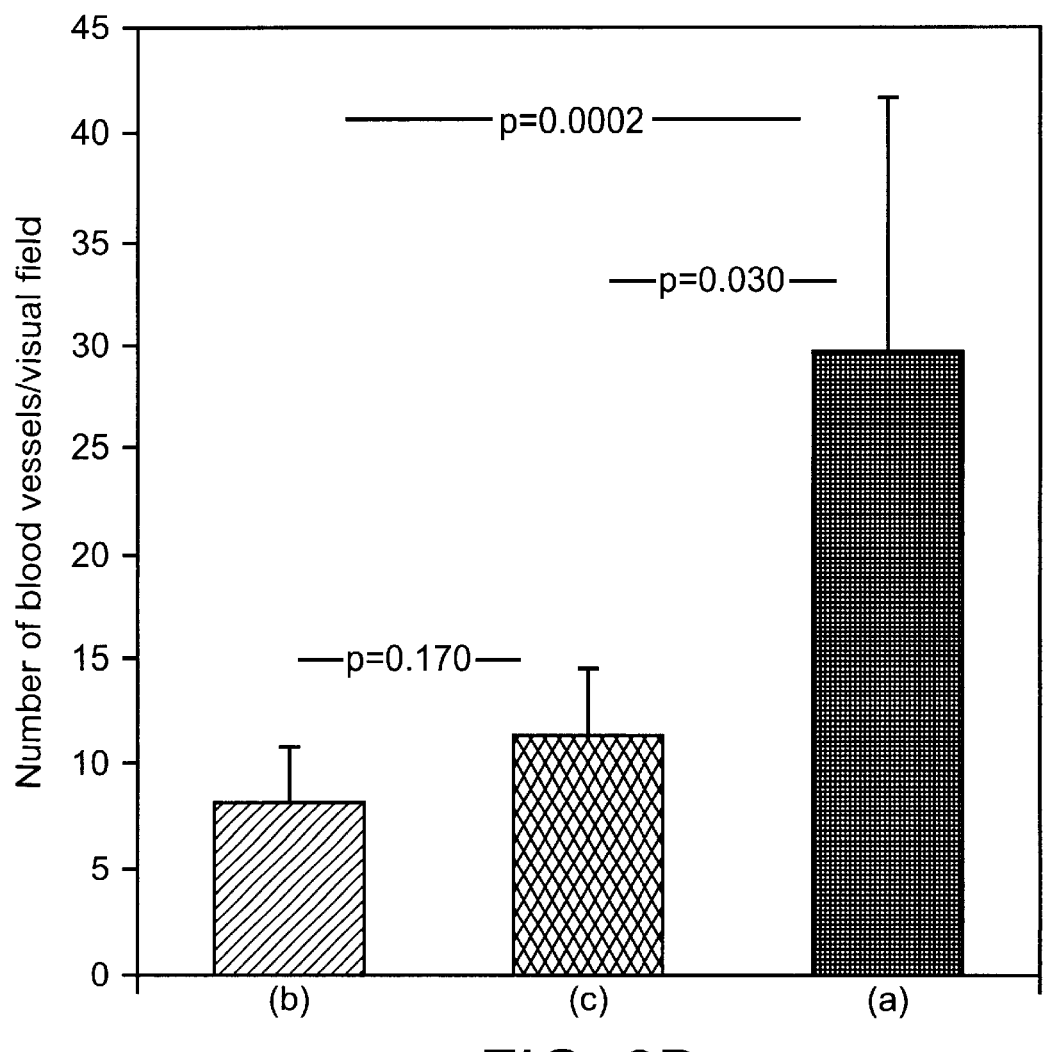
FIG. 2B shows the number of blood vessels by way of a diagram.
Figures 1, 3A:
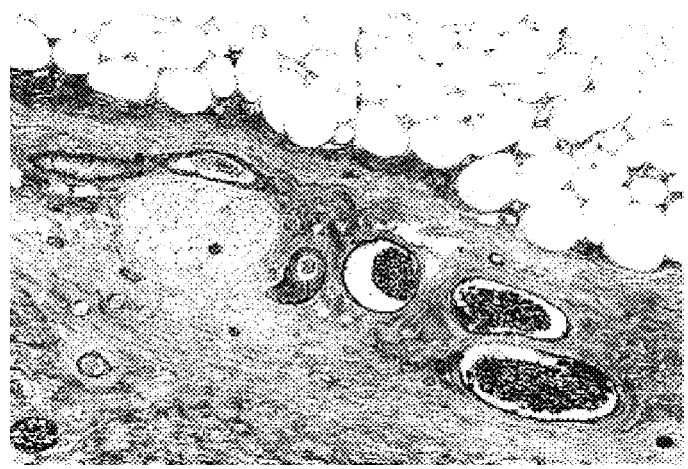
Figures 2, 3A:
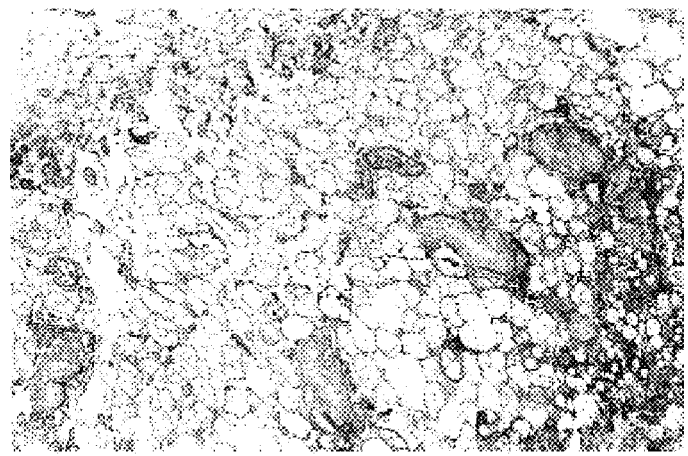
Figures 3, 3A:
Figure 3B:
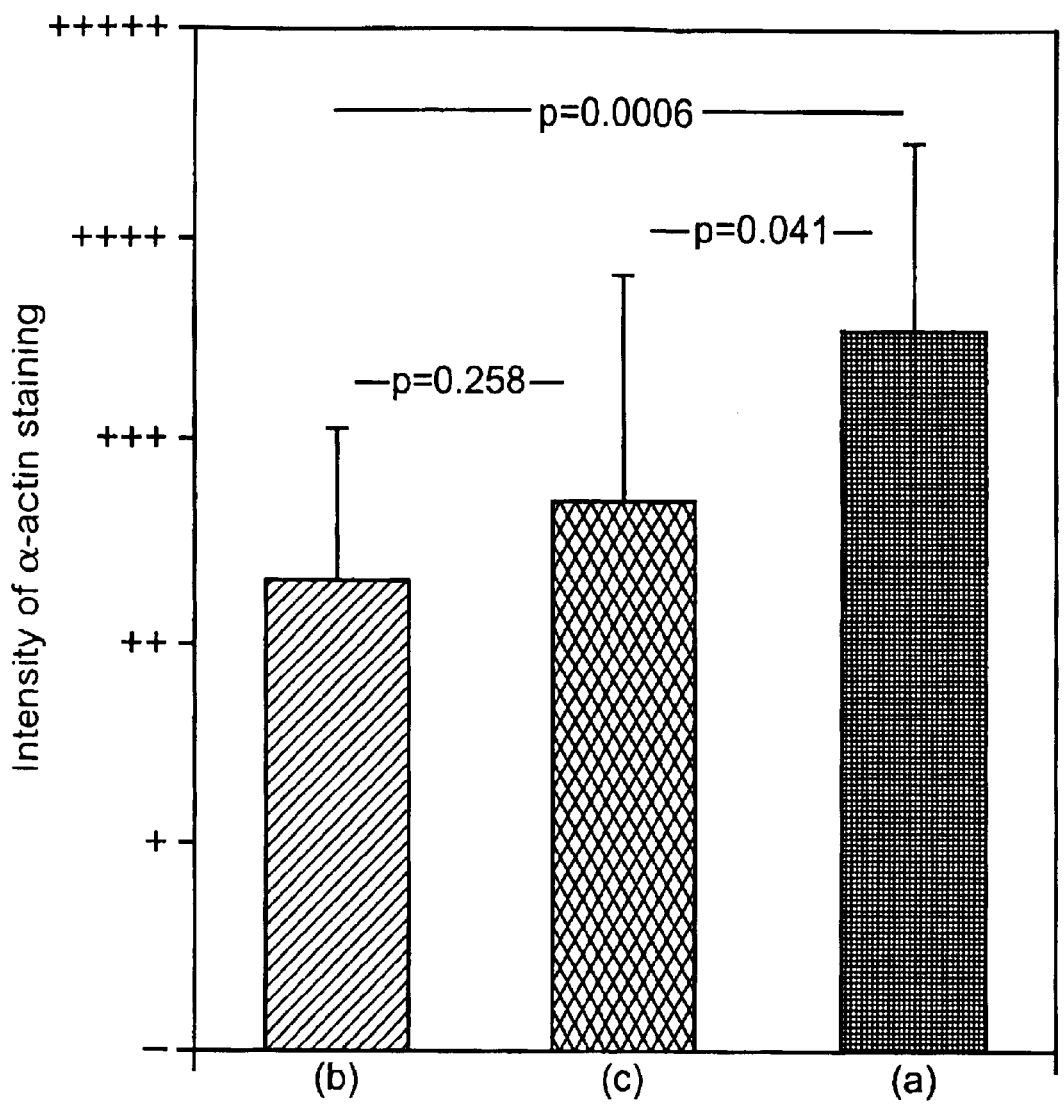
FIG. 3B shows the strength of the staining by way of a diagram.

It is the object of the present invention to provide a product by means of which the above objective can be achieved. According to the invention this is achieved by the subject matters defined in the claims.

Thus, the subject matter of the present invention relates to the use of tissue factor for influencing blood vessel formation, in particular for activating blood vessel formation, above all for wound healing.

The present invention is based on the applicant's finding that in wounds of animals tissue factor results in the formation of vessels (blood vessels). He found out that the vessels comprise endothelial and smooth muscle cells. The applicant also recognized that wound healing can be achieved by means of tissue factor. Furthermore, the applicant discovered that vessel formation can be prevented by inhibiting tissue factor.

Tissue factor is a transmembrane glycoprotein which binds the blood clotting factors VII and VITa, respectively. An activation of the blood clotting factors X and IX, respectively, is effected by this bond, so that the blood coagulation is started via the extrinsic path and intrinsic path, respectively. Tissue factor has a molecular weight of 43 to 46 kD. Its primary structure is known as is the gene for tissue factor and its localization on the chromosome. Scarpati et al, 1987, *Biochemistry* 26:5234–5238.

According to the invention tissue factor is used for activating vessel formation, particularly for wound healing. The expression "tissue factor" relates to a tissue factor of any kind and origin. It may be an animal or human tissue factor. It can be glycosylated or non-glycosylated. Also, it may be a fragment of tissue factor which is capable of forming vessels, in particular for wound healing. The tissue factor can have a wild-type sequence. Its sequence can also differ from the wild-type sequence by one or several amino acids. In addition, the tissue factor can be part of a fusion protein.

In a preferred embodiment, the tissue factor is present in the form of an expressible nucleic acid. It may be a DNA and/or RNA, a DNA, particularly a genomic or cDNA and fragments thereof, respectively, being preferred. The above statements made on the tissue factor apply here correspondingly to the nucleic acid.

The expression of the nucleic acid can be achieved as usual. It can be favorable for the nucleic acid, e.g., as a DNA, particularly cDNA, to be present in a vector which is suitable for expression in animal cells. A person skilled in the art is familiar with such expression vectors. For example, they may be virus or plasmid vectors. It is advantageous for the vectors not to integrate into the genome of cells but remain episomally within the cells. By this, a transient expression of the tissue factor is achieved, which is preferred. The nucleic acid as a DNA, particularly cDNA, can also be controlled by a constitutive or inducible promoter. An inducible promoter can be, e.g., tissue-, organ- and/or tumor-specific. It can be favorable for the nucleic acid as DNA, particularly cDNA, to be controlled by the CMV promoter, e.g., in the expression vector pcDNA3 (Invitrogen company) or controlled by the SV40 promoter, e.g., in the expression vector pSVK3 (Pharmacia company). Such expression plasmids referred to as pcDNA3-TF (tissue factor) and pSVK3-TF, respectively, also represent a subject matter of the present invention. It can be particularly advantageous for the nucleic acids as DNA, particularly cDNA, to be present in a Sindbis virus replicon vector. Such a vector permits an extremely high expression of the nucleic acid. An example of such a vector is the ELVS vector system from Viagene Inc. An expression plasmid referred to as ELVS-TF (tissue factor) also represents a subject matter of the present invention. For the preparation of an above vector, a person skilled in the art will use known methods. Reference is made to Maniatis et al., 1982, Molecular Cloning, A Laboratory Manual, Cold Spring Harbor Laboratory, by way of supplement.

According to the invention tissue factor is used for activating vessel formation, in particular for wound healing. The expression "vessel formation" relates to a vessel formation of any kind and at any site. For example, it relates to a vessel formation serving for replacing impaired,. e g., old, blood vessels. They can be present, e.g., in the brain or heart, so that an apoplexy or infarction can be prevented or treated. Precautions can also be taken against presbyphrenia. In addition, it relates to a vessel formation for treating arteriosclerosis, Crohn's disease and ulcerative colitis, diabetic retinopathy and deep venous thrombosis of the legs/ulcus cruris as well as the prevention of relapses. In particular, it is relates to vessel formation and wound healing. The expression "wound healing" relates to wound healing of any kind and at any site. It can be normal and impaired wound healing. The latter is found in particular in the case of diseases, such as diabetes mellitus, vasculitis, arterial occlusive disease, chronic venous and/or infected ulcer as well as poorly healing gastric ulcer. Impaired wound healing is also found in the case of innervation impairment such as paraplegia, leprosy, neuropathy, etc., and decubital gangrene of persons in need of care. Impaired wound healing will also be given if weak sutures and impaired healing occur after operations, particularly of the intestines and transplantations of skin and other organs, respectively. Impaired wound healing is also found in the case of bone fractures, burns and treatments using steroids.

According to the invention tissue factor is administered in the form of a protein or an expressible nucleic acid to activate vessel formation, in particular for wound healing. It may be favorable for the tissue factor to be administered in combination with further factors supporting vessel formation, in particular for wound healing, such as vascular endothelial growth factor (VEGF). These factors can also be present in the form of proteins and/or expressible nucleic acids. The tissue factor and said factors can be administered simultaneously or successively. The kind of administration of tissue factor alone and together with said factors, respectively, can orient itself by the site of action, i.e., at the site where blood vessel formation, in particular for wound healing, shall take place. For example, it is an obvious thing to treat an area on the body surface locally and one within the interior of the body systemically. Common methods can be used for the administration of tissue factor alone and together with said factors, respectively. For the local administration it is, e.g., favorable to pack the factor or factors into liposomes or absorb them onto carriers, particularly gold particles, and apply the liposomes to the corresponding site of the body and shoot the carriers, particularly gold particles, into the tissue, respectively. Furthermore, pharmaceutical compositions are provided for the administration of tissue factor alone and together with said factors, respectively, which may contain common auxiliary substances such as carriers, solvents, etc. Such compositions also represent a subject mater of the present invention.

According to the invention tissue factor is also used for inhibiting blood vessel formation. For this purpose, the tissue factor can be present in the form of an antibody inhibiting it. The tissue factor can also be present in the form of a nucleic acid which has an antisense effect on the expression of tissue factor. In particular tumoral diseases can be treated by the inhibition of vessel formation.

By means of the present invention it is possible to influence vessel formation. In particular, vessel formation can be activated. The resulting blood vessels comprise endothelial and smooth muscle cells. Thus, the present invention is suited for the prevention and treatment of the most varying diseases. Examples thereof are indicated above. In particular, the present invention is suitable for the treatment and/or prophylaxis of impaired wound healing, above all in the case of diabetes mellitus, where it is possible to heal large open wounds located at the extremities. In addition, vessel formation can be inhibited by means of the present invention. Thus, the present invention is also suited to treat diseases, such as tumoral diseases. The present invention makes a major contribution to modern medicine.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

EXAMPLE

Preparation of a Tissue Factor-expressing Plasmid and its use for Influencing Blood Vessel Formation, Particularly for Activating Blood Vessel Formation, Above All for Wound Healing (A) The entire translated region (1.8 kb) of the mouse tissue factor gene was integrated into the BamHI site of the multiple cloning site of pcDNA3 (Invitrogen). Thus, this region was controlled by the CMV promoter. The expression plasmid pcDNA3-TF was obtained. In the same way, the coding region (0.7 kb) of the mouse tissue factor gene was integrated in the antisense orientation into the EcoRI site of the multiple cloning site of pcDNA3. Thus, this region was also controlled by the CMV promoter. The expression plasmid pcDNA3-TF-AS was obtained.

6 mm full thickness wounds each were placed on the backs of three female NOD mice (Bomholtgaard, Denmark) at a distance of 8 to 10 mm. These wounds were treated with mixtures containing 2 μg pcDNA3-TF (a), pcDNA3-TF-AS (b) and pcDNA3 (control (c)), respectively, and 12 μg DOTAP transfection reagent (Boehringer Mannheim) each. The wounds were covered with Ohmann Opraflex.

For proving the formation of vessels (blood vessels) in the wounds, 300 μl of ink (Nigrosin, Sigma) each were injected into the caudal vein of the mice 6 days and 8 days, respectively, following the administration of the mixtures. Thereafter, the animals were killed and the skin regions with the wounds were examined under a microscope.

It showed that if a tissue factor-expressing vector (a) is administered, vessels (blood vessels) will be formed in wounds and thus wound healing will be promoted. It also turned out that an antisense tissue factor can inhibit the formation of blood vessels.

(B) As described under (A), six NOD mice were treated. After 6 days and 8 days, respectively, the animals were killed and the corresponding skin regions were examined under a microscope after having been subjected to α-actin staining (with Sm-actin antibodies from Dianova).

It showed that the blood vessels formed comprise smooth muscle cells.

All references cited within the body of the instant specification are hereby incorporated by reference in their entirety.

What is claimed is:

1. A method of activating blood vessel formation in a subject in need, comprising locally administering a functional Tissue Factor in a therapeutically effective amount to a non-malignant tissue of said subject in need, wherein said Tissue Factor or a fragment thereof is administered in the form of an expressible nucleic acid present in a plasmid vector; and wherein the administration of the functional Tissue Factor causes activation of blood vessel formation in the non-malignant tissue.

2. The method of claim 1, wherein said nucleic acid is expressed transiently.

3. The method of claim 1, wherein said nucleic acid is a DNA.

4. The method of claim 1, wherein said nucleic acid is controlled by a constitutive or an inducible promoter.

5. The method of claim 1, wherein said nucleic acid is controlled by a CMV or SV40 promoter.

6. The method of claim 1, wherein the said subject in need is afflicted with diabetes mellitus, vasculitis, arterial conclusive disease, chronic venous and infected ulcer, innervation impairment, decubital gangrene or weak sutures after a surgery.

7. The method of claim 1, wherein said subject in need is afflicted with arteriosclerosis, Chroh's disease, ulcerative colitis, diabetic retinopathy, or deep venous thrombosis of the legs ulcus cruris.

8. The method of claim 1, wherein the blood vessel formation is activated for the replacement of impaired blood vessels.

9. A method for enhancing wound healing in a subject in need, comprising locally administering a Tissue Factor or a fragment thereof in the form of an expressible nucleic acid present in a plasmid vector to a non-malignant wound tissue of said subject in need.

10. The method of claim 1 or 9, wherein said plasmid vector is present in a liposome or on a carrier.

11. The method of claim 10, wherein said carrier is a gold particle.

12. The method of claim 1 or 9, wherein said plasmid vector is present in a pharmaceutical composition.

13. The method of claim 12, wherein said plasmid vector is present in combination with further factors promoting the formation of blood vessels.

14. The method of claim 13, wherein said further factors are present as expressible nucleic acids or functional proteins.

15. The method of claim 14, wherein at least one further factor is present and said further factor is VEGF.

* * * * *